United States Patent
Shehata

(10) Patent No.: US 8,167,870 B2
(45) Date of Patent: May 1, 2012

(54) APPARATUS AND METHOD FOR THE CONTROLLED HYDRODISTENTION OF THE URINARY BLADDER

(76) Inventor: Sobhy Shehata, Palm Harbor, FL (US)

(*) Notice: Subject to any disclaimer, the term of this patent is extended or adjusted under 35 U.S.C. 154(b) by 418 days.

(21) Appl. No.: 12/571,594

(22) Filed: Oct. 1, 2009

(65) Prior Publication Data

US 2010/0016839 A1 Jan. 21, 2010

Related U.S. Application Data

(62) Division of application No. 11/586,458, filed on Oct. 25, 2006, now Pat. No. 7,615,046.

(51) Int. Cl.
*A61M 27/00* (2006.01)
*A61M 35/00* (2006.01)
*A61M 31/00* (2006.01)
*A61M 25/00* (2006.01)
*A61M 1/00* (2006.01)

(52) U.S. Cl. .......... 604/544; 604/289; 604/67; 604/264; 604/509; 604/31

(58) Field of Classification Search .................. 604/408, 604/544, 509
See application file for complete search history.

(56) References Cited

U.S. PATENT DOCUMENTS

| | | | | |
|---|---|---|---|---|
| 4,230,102 A | * | 10/1980 | Ekbladh | 606/192 |
| 4,332,378 A | * | 6/1982 | Pryor | 482/68 |
| 4,718,425 A | * | 1/1988 | Tanaka et al. | 600/486 |
| 4,793,351 A | * | 12/1988 | Landman et al. | 606/195 |
| 5,069,050 A | * | 12/1991 | Chen | 70/456 R |
| 5,286,259 A | * | 2/1994 | Ganguly et al. | 604/96.01 |
| 5,304,214 A | * | 4/1994 | DeFord et al. | 607/105 |
| 5,318,891 A | * | 6/1994 | Elgebaly | 435/7.24 |
| 5,370,675 A | * | 12/1994 | Edwards et al. | 607/101 |
| 5,509,929 A | * | 4/1996 | Hascoet et al. | 607/101 |
| 5,514,092 A | * | 5/1996 | Forman et al. | 604/101.03 |
| 5,867,839 A | * | 2/1999 | Lawlor | 2/240 |
| D439,202 S | * | 3/2001 | Takabayashi | D11/215 |
| RE37,704 E | * | 5/2002 | Eshel | 604/113 |
| 6,382,214 B1 | * | 5/2002 | Raz et al. | 128/898 |
| 6,432,081 B1 | * | 8/2002 | Atala | 604/103.08 |
| 6,447,505 B2 | * | 9/2002 | McGovern et al. | 606/41 |
| 6,461,332 B1 | * | 10/2002 | Mosel et al. | 604/174 |
| 6,524,268 B2 | * | 2/2003 | Hayner et al. | 604/8 |
| 6,579,247 B1 | * | 6/2003 | Abramovitch et al. | 600/587 |
| 6,682,555 B2 | * | 1/2004 | Cioanta et al. | 623/1.21 |
| 2004/0267340 A1 | * | 12/2004 | Cioanta et al. | 607/105 |
| 2005/0065468 A1 | * | 3/2005 | Goebel | 604/96.01 |
| 2005/0080399 A1 | * | 4/2005 | Bolmsjo et al. | 604/509 |
| 2007/0073216 A1 | * | 3/2007 | McAuliffe et al. | 604/30 |

* cited by examiner

*Primary Examiner* — Leslie Deak
*Assistant Examiner* — Susan Su
(74) *Attorney, Agent, or Firm* — Dennis G. LaPointe

(57) ABSTRACT

A urological medical system for performing a controlled hydrodistention of the urinary bladder for treating a bladder dysfunction problem comprised of a programmed CPU with associated computer equipment for facilitating an automatic control of a treatment procedure to be performed on a patient, a saline solution warmer, a saline solution pump, a four-way catheter wherein a channel is provided for monitoring the pressure within the bladder during the procedure, a syringe for infusing a medicine through the catheter and a strapping device to secure the syringe and to slidingly engage the catheter to a leg of the patient. Desired parameters are monitored during the procedure and a desired pressure is maintained in the bladder for a predetermined time to perform the controlled hydrodistention of the urinary bladder.

11 Claims, 4 Drawing Sheets

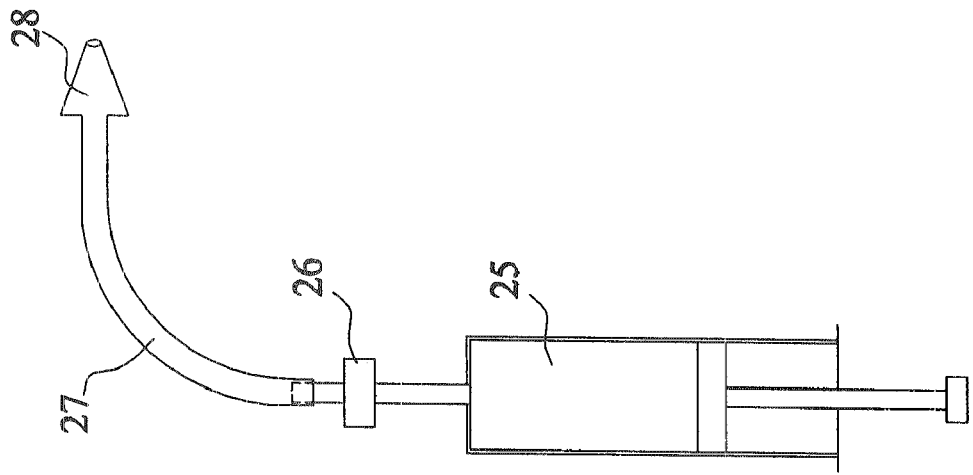
Fig.3
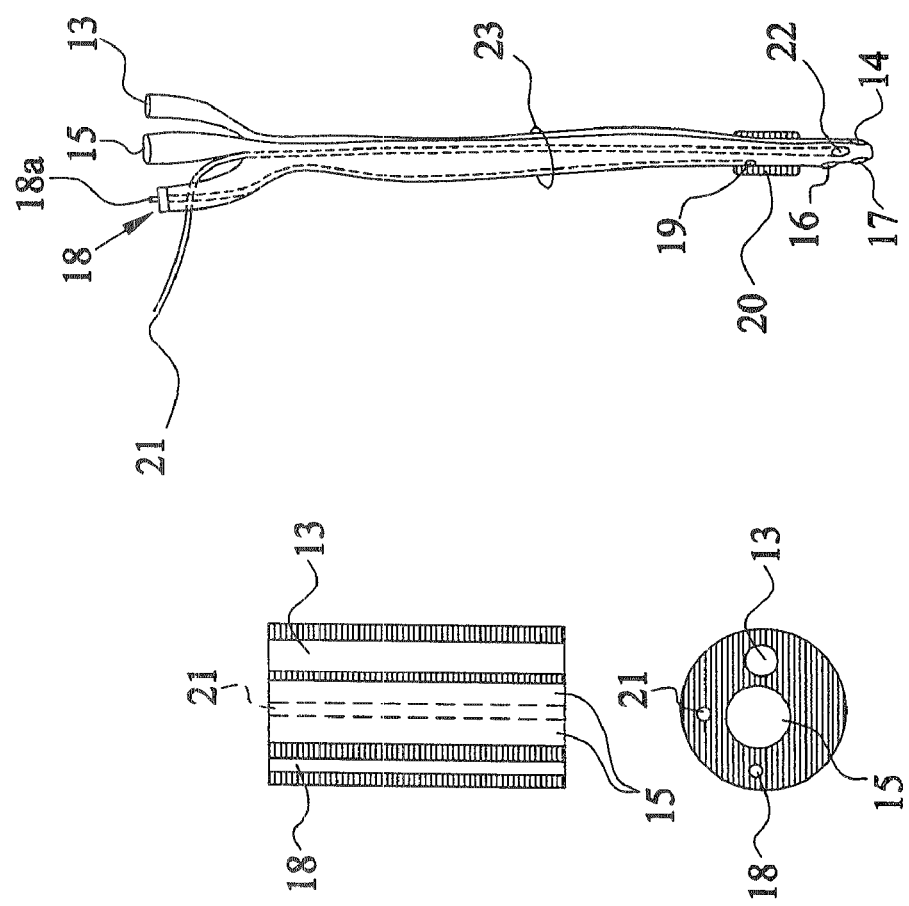
Fig.2A
Fig.2B

APPARATUS AND METHOD FOR THE CONTROLLED HYDRODISTENTION OF THE URINARY BLADDER

RELATED APPLICATION

This application is a divisional application of U.S. patent application Ser. No. 11/586,458 filed Oct. 25, 2006.

FIELD OF THE INVENTION

The invention relates to a novel system and method that is capable of performing controlled hydrodistention of the bladder with a closed and sterile system with an integrated predetermined set of scientific standards and controlled parameters for treatment of multiple common bladder dysfunction problems.

BACKGROUND OF THE INVENTION

The urinary bladder dysfunction problems are widespread and common. The symptoms could range from mild irritative ones in the early stage of various diseases to the debilitating ones in the later stages of the disease. The symptoms usually include urinary frequency, urgency and nocturia (waking up at night to go to the bathroom to void) with or without urge incontinence. Therefore the need to increase awareness amongst the medical community as well as the public about the availability of treatment for those ailments would dramatically improve the people's quality of life since early intervention will obtain good results as well as arresting the progression of disease, which in turn will prevent reaching the refractory and debilitating conditions that has the potential to incapacitate many people.

Urinary Bladder Dysfunction Problems that could Benefit from the invention described below which deals with the Controlled Hydrodistention of the Bladder (CHDB):
1. Overactive Bladder (OAB) Subsets of this Disorder Include:
   a) Overactive bladder dry
   b) Overactive bladder wet
   c) Refractory overactive bladder The symptoms of overactive bladder (OAB) include urgency, frequency and nocturia with or without urge incontinence. Urgency is defined as the sudden compelling desire to void that is difficult to defer. It is estimated that 17% of the population or about 33 million Americans experience symptoms of overactive bladder. The diagnosis can be made after complete history and physical examination, urinalysis, review of the bladder diary, measurement of post void residual urine, cytology, uroflowmetry and cystoscopy. Organic causes of urinary symptoms should be ruled out such as urinary tract infection, stones, obstruction and cancer etc. Urologists are familiar with the workup of the evaluation and management of those problems. Once overactive bladder diagnosis is made, then behavior modification in the form of fluid intake restrictions and pelvic floor exercises in addition to controlled bladder hydrodistention should help many of those patients in alleviating their distressing symptoms.

The current treatment used nowadays and the drawbacks:
   a. Antimuscarinic medications may help in some patients; however the disadvantages include high cost, tolerance which requires increase of the dosage or change of the medicine and multiple side effects that include dry mouth, constipation, dizziness, confusion and loss of the brain cognitive function especially in the elderly population and potential cardiac side effects. All of the above lead to high percentage of drop outs. In fact, it is estimated that out of one thousand patients taking medication, only two hundred will continue medication after one year, a mere 20%, in other words, the drop out percentage rate is about 80%. Our novel device would eliminate all those potential side effects and complications.
   b. Neuromodulation (Interstim) an invasive, costly, surgical procedure with limited effectiveness and in many cases disappointing long term results.
   c. Botox involves injection of Botulinum toxin into the bladder (not FDA approved as of the date of this patent application) is a costly, invasive procedure with lack of uniform results and potential complications such as muscle weakness, aggravation of symptoms following multiple injections, and development of resistance.
   d. Highly invasive and costly surgical procedures that occasionally are used in advanced debilitating conditions. Those procedures include augmentation cystoplasty, detrusor myomectomy, and cystectomy with diversion. All those procedures are extremely invasive and carry with them the potential risks and complications of major surgery. Our novel device should help many of those patients and could be an integral part of multimodal approaches to the difficult problems. However, we must stress here again that the increased awareness should allow many patients problems to be handled in their early stages when their results are better and more sustainable.

In brief, controlled hydrodistention of the bladder (CHDB) as a first line intervention in overactive bladder may actually produce an affect on unmyelinated C-fibers in the bladder producing local differentiation and thus help the overactive bladder symptoms. The potential risks of hydrodistention of the bladder may involve infection which can be reduced by antibiotic premedication, transient hematuria which usually subsides spontaneously. A bladder tear should be extremely rare since the entire procedure is performed under a strict set of scientific parameters and the fact that the entire procedure is performed with a sterile and closed system should allow simple catheter drainage to be all that is needed to handle this complication should it ever occur.

2. Interstitial Cystitis (IC) and Chronic Pelvic Pain Syndrome (CPPS) in Women.

This common syndrome is characterized by the symptoms of urgency and frequency of urination in addition to pelvic pain. It is estimated that 38% of women presenting to their physician for chronic pelvic pain syndrome have interstitial cystitis. CPPS is believed to occur in as many as 1 in 4.5 women in the USA. The total annual cost for CPPS was estimated in 1996 to be approximately 2.8 billion dollars in addition to about 500 million dollars in lost work time. The symptoms range from mild early on to severely debilitating in advanced cases. The symptoms could include generalized pelvic pain in the lower abdomen, urethra, perineum, pain with intercourse and pain with bladder filling. The voiding symptoms include frequency, urgency, nocturia and premenstrual exacerbations. The results are reduced quality of life, emotional distress, depression and disruption of normal activities and social relationships. Several treatment approaches are used to manage IC/CPPS including cystoscopy and hydrodistention of the bladder under anesthesia, however the lack of scientific standards and the lack of control parameters limit the use of this procedure. Since there have been no standard methods of bladder hydrodistention, the results vary markedly, and make it difficult to replicate the better results of some centers. The use of our novel device would in effect introduce the scientific and standard parameters required to replicate the good results in various centers by different operators. We should again emphasize that the increased awareness of using the novel device in the early stages of this disease could help immensely with many patients, as well as the potential to arrest the disease progression.

3. Chronic Prostatitis (CP) and Chronic Pelvic Pain Syndrome (CPPS) in Men.

Other terminology includes chronic nonbacterial prostatitis and prostatodynia. There is an understanding that CP/CPPS is a form of IC/OAB syndrome. The predominant symptom is pain most commonly localized to the perineum suprapubic area and penis. It can also occur in the testes, groin or low back. Pain that occurs during or after ejaculation is the dominant symptom in some patients. Many patients experience lower urinary tract symptoms (LUTS) in the form of urgency, frequency, hesitancy in addition to poor and interrupted flow of urine. Some patients will also experience erectile dysfunction (ED). Many of these patients have significant impairment of the quality of life. Currently there is no uniformly effective treatment, and hence the prolonged suffering of those patients. The use of multiple ineffective medications leads to considerable drop in the quality of life, decreased productivity, depression and other social problems. The novel device should help many of those patients ameliorate symptoms and put many of them on the road to recovery. Again we must stress that public awareness and early interference should reward many of those patients with improvement in all aspects of their life.

4. Mixed Urgency and Stress Urinary Incontinence in Females

Stress urinary incontinence is defined as loss of urine control upon increase in intra abdominal pressure, such as in coughing, sneezing or heavy lifting. This is a very common urologic problem in female patients. However, if the stress incontinence is associated with urinary frequency, urgency and nocturia with or without urgency incontinence, now the condition is termed mixed urgency and stress urinary incontinence. It is understood that this is a combination of stress urinary incontinence and overactive bladder (OAB). Once the patient evaluation is completed and other organic causes are ruled out and the overactive bladder symptoms are the predominant feature, then surgical intervention to correct the stress urinary incontinence component may not be helpful at all. In fact, it could intensify that patient's symptoms, therefore in this category of patients treatment should be directed at the overactive bladder component. Controlled hydrodistention of the bladder (CHDB) will help control the OAB symptoms and in fact could improve the stress urinary incontinence component and avoid unnecessary and potentially harmful surgical intervention. In addition, for those patients who had surgical intervention for the stress incontinence component, using the novel device to perform controlled hydrodistention of the bladder could help in controlling the urgency incontinence component. Large scale clinical studies again should standardize the approach and validate the procedure.

5. Benign Prostatic Hypertrophy (BPH) Associated with Overactive Bladder (OAB)

It is understood that BPH occurs in 50% of male patients age 50, in 60% of male patients age 60, 70% of male patients age 70 and 80% of male patients age 80. Approximately 50% of male patients with BPH have symptoms related to overactive bladder (OAB). They symptoms of frequency, urgency with or without urge incontinence, as well as nocturia should alert the treating physician of the existence of OAB in these patients. When the complete clinical evaluation reveals no bladder outlet obstruction or minimal to borderline bladder outlet obstruction from the prostate, the rush to perform ablative surgery for the prostate could have detrimental consequences by adding post prostatectomy urinary incontinence, in addition to the overactive bladder symptoms. When the clinical evaluation reveals that the OAB symptoms predominate or when the situation is borderline, the use of the novel device and performing CHDB could improve the patient's symptoms and avoid unnecessary surgery and its potential complications and expense. The availability of the novel device will assist in conducting proper large scale clinical studies to further validate its usefulness in such patients. Controlled hydrodistention of the bladder could also be used in the unfortunate patient who already had prostate surgery and continues to have the OAB symptoms, therefore avoiding the use of medications with the inherent expense and side effects.

6. Nocturnal Eneuresis and Diurinal Eneuresis in Children and Adolescents

Eneuresis is defined as involuntary voiding, nocturnal eneuresis is nighttime bedwetting, and diurinal eneuresis is daytime wetting. Nocturnal eneuresis occurs in approximately 15% of children at age 5. By age 7, children are expected to be dry. Nocturnal eneuresis is approximately 50% more common in boys than in girls. The complete clinical evaluation should disclose any organic causes of eneuresis. Once no organic cause is found, it is believed that those patients have an element of OAB. Similar conclusions could be drawn from the clinical workup of patients with diurinal incontinence. Currently the available treatment includes medications such as Imipramine and DDAVP Desmopressin. Side effects of Imipramine may include sleep disturbance, appetite changes, GI symptoms, nervousness and personality changes which could lead to termination of treatment. DDAVP adverse effects could range from nasal irritation when nasal spray is used, to potential serious effect of water intoxication and hyponatremic seizures, again leading to discontinuation of therapy. Many physicians use those medications in addition to bladder training and conditioning therapy using a urinary alarm; however the results are usually modest. Frustration of the child and parents could develop due to the prolonged management, lack of success and considerable treatment side effects. Here again, the use of our novel device and performing CHDB could have far better results. Again large scale properly conducted clinical studies should validate the device's usefulness and establish the scientific standards and parameters for this approach.

SUMMARY OF THE INVENTION

The invention is a novel urological medical device or system and associated procedure designed to use automated, calibrated, electronic equipment to perform controlled hydrodistention of the urinary bladder (CHDB) for the purpose of treating multiple bladder dysfunction problems that are extremely common and widespread affecting millions of Americans, as well as millions worldwide. Urinary bladder dysfunction problems lead to marked diminution of quality of life associated with significant drop in productivity, diminished self esteem and billions of dollars lost to various treatments associated with considerable side effects, complications and lack of uniform success, in addition of the loss associated with decreased work productivity.

In particular, the idea relates to a novel automated device to perform controlled bladder hydrodistention, the purpose of which is the creation of a device characterized by development of scientific and standardized parameters, in addition to built-in safety guards to allow replication of the medical procedure by different physicians and qualified technical operators after a short course of training. This novel device will also allow uniform standards to conduct various clinical studies to verify the effectiveness of controlled bladder hydrodistention (CHDB) in several widespread and common ailments, collectively called bladder dysfunctions. This approach once becomes public knowledge with increased awareness amongst the medical community as well as the public at large, has the potential not only to treat the various urological ailments, but also could arrest the progression of many diseases and avoid the debilitating effects of these diseases.

Some of the components that comprise the invention equipment/system include:

1. A cart on wheels to facilitate transportation of the equipment in and around the medical facility, in a doctor's office, or in surgery centers and hospitals.
2. A central processing unit (CPU) with software, also referred to herein as central microprocessing means, which can show the various parameters of the procedure including the fluid infusion rate, the volume infused, the pressure in the bladder and the procedure time, in addition to the specific scientific parameters, standards and limitations each step of the way. Given the parameters to be monitored and the interface components such as the pump and warmer, one skilled in the art of programming can write the source code necessary to operate the computerized system.
3. A computer monitor that can display all the above mentioned parameters in graphical format.
4. A keyboard and mouse.
5. An automatic solution warmer to bring the temperature of the infused fluid (normal saline) to the body temperature with the ability to bring the temperature up or down for the purpose of conducting various future clinical studies.
6. An electronic pump that is automatically controlled to allow the preset infusion rate, monitor the volume infused and to create controlled pressure inside the bladder so that the pressure will not exceed desired or predetermined levels.
7. A printer for procedure documentation and a follow up review.
8. A holding pole to carry the infusion fluid (normal saline) bag.
9. Various connecting tubing.
10. A tube holder to carry the tube from the pump which will connect to a four way balloon catheter that will be inserted inside the patient's bladder through the urethra. That tube holder should be vertically adjustable, such as adapted to slide on a pole that can bring it up and down, for adjusting the tube height to the level of the patient's symphysis pubis. This in effect should ensure that the tubing will not get kinked, and at the same time, take up any slack in the tubing between the pump and the four way balloon catheter.
11. An additional feature of the novel device can include a manual override that can perform the following functions if necessary:
    a) Stop the inflow of fluid into the bladder.
    b) Increase the fluid volume.
    c) Terminate the procedure.
    d) Change the infusion rate.
    e) Change the time of infusion.
    The manual override control function can be programmed to be operated from the keyboard or the display itself can be a touch control display such as those typically seen in restaurants computer systems or a separate associated hardware component control can be incorporated such that when functionally activated, the programming will recognize the override to allow for the physician to take over control of the procedure.
12. Means for inputting data before the procedure starts, including patient's name, age, sex, diagnosis, date of the procedure and clinical remarks.

The novel four way balloon catheter is an integral part of the invention and is used to perform the controlled hydrodistention of the bladder (CHDB). The size is 18 French for adults and 14 French for pediatrics. The catheter integrates four different channels described as follows:

1. A channel for balloon inflation that accommodates 20 cc of sterile water. The purpose of the balloon is to be gently pulled snug against the bladder neck to create a closed bladder capable of sustaining a predetermined intravesical pressure without leakage.
2. A small infusion channel to allow the infusion of medications into the bladder. This channel would be connected to a 50 cc syringe via non-kink tubing with a lock, as well as an adapted "Christmas tree" end that fits tightly into the infusion channel port. The lock will help to retain the fluid inside the bladder and maintain the necessary bladder pressure. This infusion port with the syringe can also be used to withdraw fluid from the bladder as an integral step in the procedure to be described later.
3. A wide central main channel to allow fluid infusion from the pump into the bladder using the predetermined infusion rate and pressure. This channel will also be used to empty the bladder prior to the initiation of the procedure, as well as complete emptying of the bladder at the end of the procedure.
4. The novel fourth channel is to accommodate a pressure sensor that is connected to the computer and extends via the catheter that ends in a pressure transducer at its tip to monitor the bladder intravesical pressure.

Now the device is a sterile and closed system under complete control by both the automated electronic equipment with the operator's ability to interfere as needed.

In particular, the invention is designed and used as a closed sterile system to perform controlled hydrodistention of the bladder integrating calibrated, electronic, high tech equipment with preset scientific standards to treat multiple and common urinary bladder dysfunction problems that will enable urologists to replicate the technical approach and the beneficial results after a short training course. The novel invention would perform the CHDB by creation of a closed and sterile system that will allow infusion of sterile normal saline warmed to the body temperature, then transferred into an automatic pump that will drive the fluid into the urinary bladder at preset computer controlled parameters which typically includes the time, the rate of fluid infusion, the volume of the fluid infused and a preset intravesical pressure. The system is fully automated with manual override to be used by the operator if necessary. The system has the capability to adjust all parameters according to the patient's particular clinical situation. There is complete monitoring of all the steps. The printer would supply a printout document for further reference in the management of each patient and to assist in performing the large scale controlled clinical studies.

Procedure:

1. The first step is the full clinical evaluation familiar to all urologists to arrive at the proper diagnosis. Urologists are familiar with the patient evaluation which could include complete history and physical, urinalysis, review of bladder diary, urine culture if necessary, uroflowmetry, measurement of post void residual, cytology if necessary, urodynamics if indicated and cystoscopy. The following diseases should be ruled out: urinary tract infection, stone disease, cancer, carcinoma in situ of the urinary bladder (CIS), obstruction due to BPH or stricture disease, hematuria workup, detection of systemic diseases that may contribute to voiding symptoms such as diabetes mellitus (DM) and heart disease. A cystogram may be necessary if reflux is suspected.

2. The procedure is explained to the patient and concerned family members, and informed consent is obtained. The patient is premedicated with a combination of oral medications, such as Diazepam 5 mg plus Hydrocodone Bitartarate 5 mg/Acetaminophen 500 mg tablet or Elixir and 250 mg of suitable oral antibiotic such as Ciprofloxacin all to be taken by the patient approximately 30 minutes before the procedure.

3. The patient is taken to the cystoscopy suite, put in the lithotomy position, prepared and draped in the usual fashion and flexible cystoscopy is performed with topical 2% Xylocaine. Once the procedure is completed and the diagnosis is confirmed, the four-way balloon catheter is inserted (18 French for adults and 14 French for pediatrics). The balloon is inflated with 20 cc of sterile water and the bladder is drained.

4. The patient position is changed to the comfortable supine position.

5. Before starting the procedure, the system should be zeroed to the atmospheric pressure and properly flushed to eliminate any air bubbles in the tubing and transducer.

6. The system could be checked further by asking the patient to cough and observe proper pressure transmittal.

7. The catheter is connected to the computer controlled system after the tubing is primed with the warm sterile normal saline.

8. The 50 cc syringe is used to mix 16 cc of 2% Xylocaine with 3 cc of 8.4% Sodium Bicarbonate and 20,000 units of Heparin.

9. The 50 cc syringe is held in position, typically against the patient's thigh and the mixture is infused into the bladder via a preferable non-kink tubing through the medicine infusion port, then locked. The mixture is allowed to stay in the bladder for approximately 5 minutes. The means for holding the syringe in place can be done in a number of ways but one preferred method is the use of a strap incorporating hook and loop fasteners with one portion that wraps around the thigh and another portion that can secure the syringe to the side of the strap. Preferably, a molded clip or receiver is attached or fixed to the strap, and adapted so that the catheter can slidingly engage within it and be generally held into position proximate to the formed Y-portion of the catheter where the branches for each infusion port are located.

10. The tube holder's horizontal level is adjusted to the level of the patient's symphysis pubis. The tube holder is preferably mounted so that it can slide vertically up or down as appropriate. It is slidingly engaged to a pole stand or preferably to a pole or bar incorporated with the table stand on which the computer equipment/printer is located.

11. The catheter outside end should be fitted into the plastic cone or clip attached to the strap, then pulled gently to keep it snug against the bladder neck to prevent leakage.

12. Titration: this is a critical step in the procedure. Now the system is completely connected and a closed sterile system is created, the procedure starts by infusing the warm normal saline at the rate of about 50 cc per minute. Therefore, the fluid from the bag runs into the warmer and into the pump, then into the bladder. All parameters should be observed carefully including the time, fluid infusion rate, the volume infused and the intravesical pressure. Communication with the patient at all times during this step is extremely important. The patient is continuously reminded to express how he feels, and once the patient indicates there is pressure in the bladder and the sensation of the desire to urinate, the patient is asked to indicate how strong those sensations are on a scale of 1 to 10 (1 is the mildest and 10 is the strongest). Once number 10 is reached, the pump is stopped and notations are taken of the time, the infused volume, and the intravesical pressure. The two parameters of the volume infused as well as the intravesical pressure, are not to be exceeded in this particular patient. During the process of fluid infusion, some patients may experience a bladder spasm or multiple bladder spasms sometimes called uninhibited bladder contractions. This would be recognized as a sudden rise in the intravesical pressure curve seen on the computer monitor; in addition the patient will experience sudden urgency and desire to urinate. As long as the rise in the intravesical pressure and the sensation of urgency are within the patient tolerance, the procedure should be continued. A recommended built-in safety guard during bladder spasms is that the pump will automatically stop if the intravesical pressure increased by 25 cm of water in 3 seconds or less. Once the bladder spasm fades away as noticed by the drop in the intravesical pressure curve as well as the decrease of the urgency and pressure felt by the patient, then the pump automatically resumes its function. However, additional clinical research may provide for changes in the safe maximum intravesical pressure to allow for maximum patient benefit in different clinical situations. The bladder spasms usually subside in about 30 seconds. It is expected that the bladder spasms occurring would be minimal owing to the moderate infusion flow rate of 50 cc per minute, the warming of the infused fluid to the body temperature in addition to the oral and intravesical premedications. (The computerized system can be programmed to temporarily stop the pump at a pre-set level, for example, as discussed above). The system is kept connected and the intravesical pressure is maintained at that same level for approximately 15 minutes. Most patients with the proper premedication and the intravesical mixture can tolerate this step well. Some patients might complain of considerable discomfort, especially pediatrics and adolescents, in this case the pressure in the bladder could be temporarily lowered by aspiration of 50 cc of fluid from the bladder using the syringe, then additional sedation could be given. A novel approach in urology patients is to use a mixture of nitrous oxide and oxygen through a nasal mask, similar to what is used in a dentist office. Once the patient becomes comfortable and relaxed, the 50 cc of fluid is reintroduced manually into the bladder and locked for the remainder of the treatment. The advantage of the nitrous oxide and oxygen system is that the communication with the comfortable patient is maintained at all times.

13. When the 15 minutes is over, the main catheter port is opened and the bladder is drained into a clean container and the volume as well as the color is inspected.

14. The catheter balloon is deflated via one of the ports, and the catheter is removed and the procedure completed.

15. A printout is made to document the entire procedure and to be used for future patient follow-up. The patient is discharged to home when fully stable and he's asked to return with a new bladder diary in approximately 6-8 weeks for follow-up and to evaluate the response to the treatment.

Now the novel system and procedure to perform controlled hydrodistention of the bladder is described and the patient selection and the various bladder dysfunction problems identified, the increase of the awareness of this novel approach amongst the medical community and the public should help millions of people improve the quality of life and increase productivity, not only in treating those bladder dysfunction problems, but also priority should be given to identifying and treating those patients with the early symptoms to arrest the progression of their disease and to prevent reaching the debilitating status which is characterized by extremely poor quality of life. It is well known that bladder dysfunction problems will not kill the patient, but it will take his/her life away.

BRIEF DESCRIPTION OF THE DRAWINGS

In the accompanying drawings:

FIG. 2A is a conceptual depiction of a four-way catheter incorporating a pressure sensor passageway or channel, a balloon inflation channel, a main infusion channel and a smaller infusion channel with associated ports;

FIG. 2B are cross-sectional depictions of the representative conceptual novel catheter of FIG. 2A;

FIG. 3 is a conceptual depiction of a 50 cc syringe with its associated tubing, Christmas tree tubing end and valve lock;

DETAILED DESCRIPTION OF THE INVENTION

Figure 1:
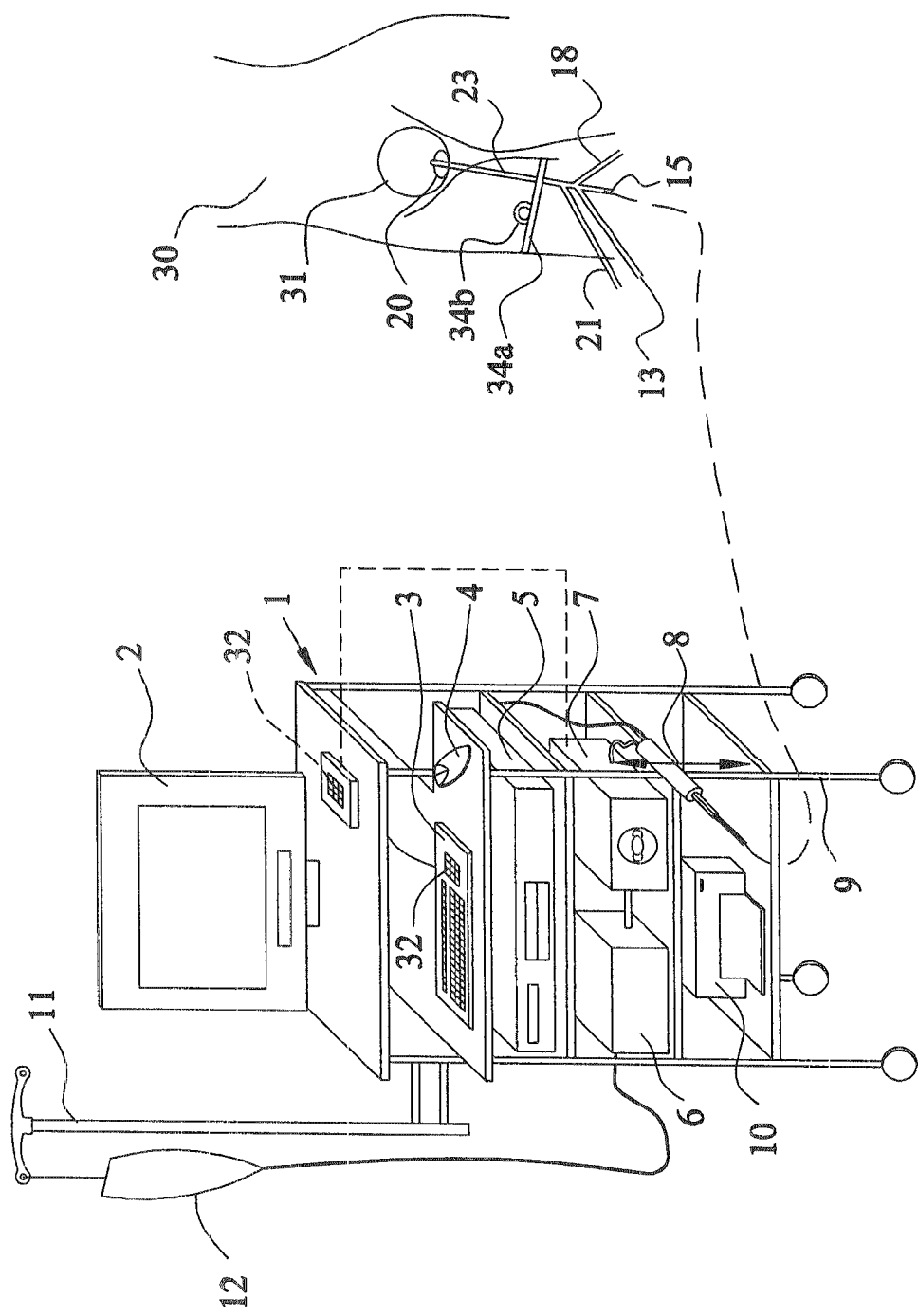
FIG. 1 is a conceptual depiction of a portable (movable) table stand for the computer processing equipment, printer, monitor, and associated accessories such as the keyboard and mouse, the warmer, the pump, the saline solution holder and vertically adjustable tube holder along with a depiction of a female patient with the novel catheter being strapped to the patient's thigh and the catheter balloon being inflated in the bladder of the patient.

Referring now to the drawings, FIG. 1 discloses one embodiment of the present invention, which is a system and procedure or process for the controlled hydrodistention of the urinary bladder, depicted generally as 100.

Figure 4:
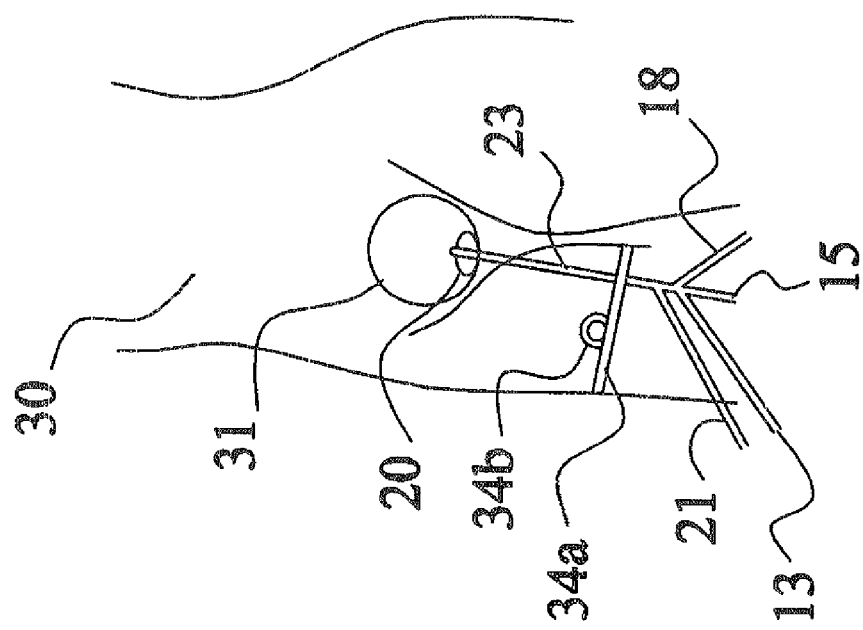
FIG. 4 is a conceptual depiction of the inventive catheter attached to a female patient as further depicted in FIG. 1.

FIG. 1 is a conceptual depiction of a portable (movable) table stand 1, typically a table with wheels and shelves for the computer processing equipment 5, printer 10, monitor 2, and associated accessories such as the keyboard 3 and mouse 4, the fluid warmer 6, the automatic pump 7, the saline solution (infusion fluid) container 12 and its holder 11, typically a pole, and a vertically adjustable tube holder 8 along with a depiction of a female patient 30 with the novel catheter 23 being strapped to the patient's thigh and the catheter balloon 20 being inflated in the bladder 31 of the female patient 30 (as also depicted in FIG. 4).

Figure 6:
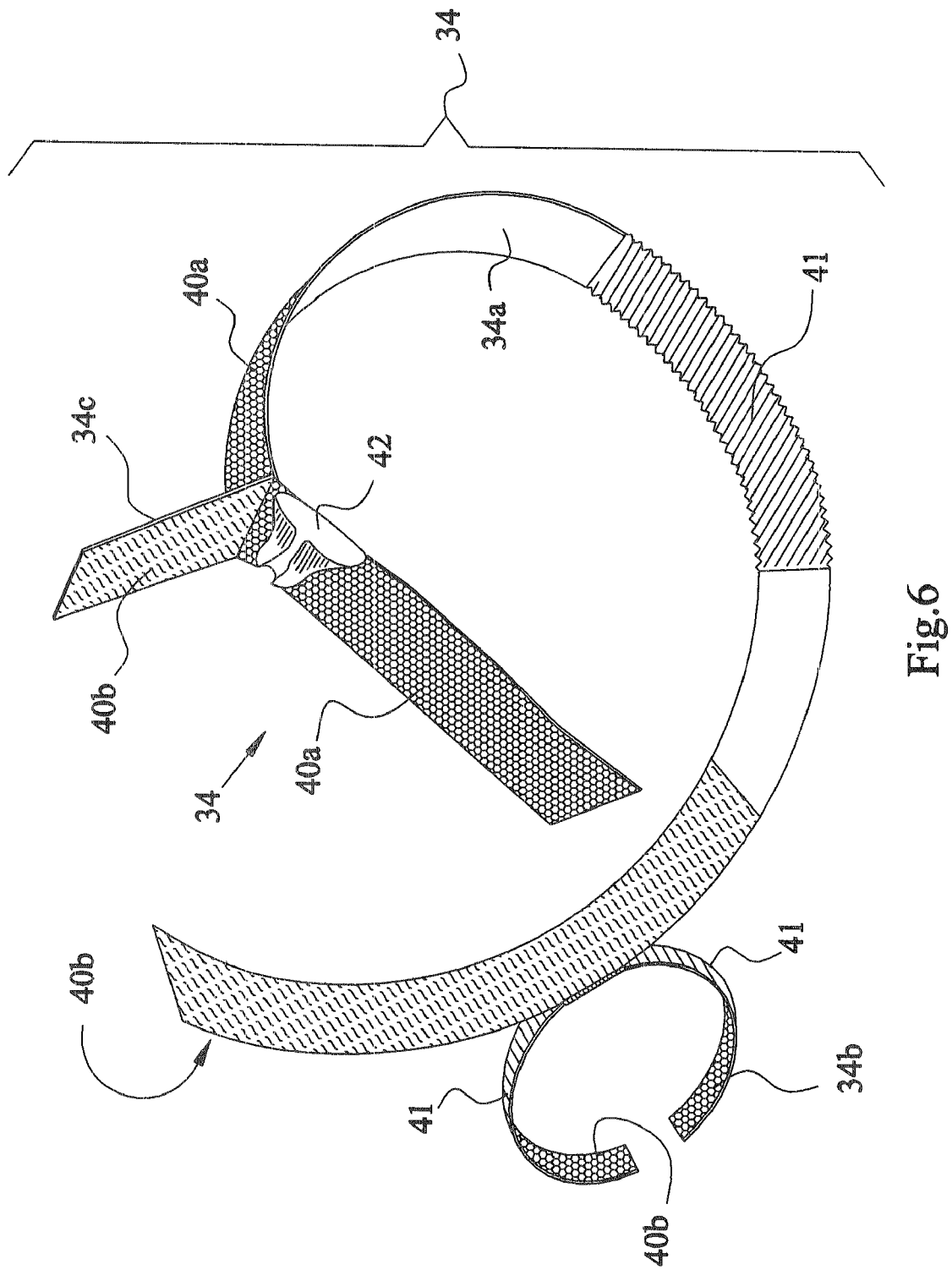
FIG. 6 is an example of an inventive strap placed around a patient's thigh for holding the catheter in place and the 50 cc syringe of FIG. 3 in place.

FIG. 3 is a conceptual depiction of a 50 cc syringe 25 with its associated tubing 27 (preferably non-kinking tubing), Christmas tree tubing end fitting 28 and valve lock 26 with an open and close handle or other operating means. The fitting 28 is adapted to connect to the infusion channel 13 of catheter 23. This syringe 25 is secured to the novel syringe and catheter holder 34 depicted in FIG. 6. The syringe holder portion or loop 34b is fixed to the main strap 34a. Strap 34a can be about 26 inches in length and have fastening means for securing around a patient's thigh. As an example of a typical fastening means, hook and loop fasteners such as those depicted in the drawing as respective mating surfaces 40a,40b are preferably used. Elastic intermediate portions 41 may also be incorporated in the holder 34 for providing additional tensioning or stretching around the syringe 25 or the thigh of the patient 30,38. A catheter holding device 42 is fixed to the strap portion 34a. This device can be a molded clip through which the catheter 23 can be slidingly engaged with the Y-neck portion of the catheter stopping at the clip 42 open end. The drawing depicts a third strap portion 34c to fold over the clip 42; however, this strap portion is optional as the main trap portion 34a can be adapted in length to overlap the clip 42.

FIG. 2A and FIG. 2B are representative of one example of a four-way catheter 23 incorporating a pressure sensor passageway or channel 21 with corresponding associated port 22 (sensor transducer port at end of pressure sensor channel 21), a balloon inflation channel 18, a main infusion channel 15 and a smaller infusion channel 13, port 14 (medicine infusion port through channel 13), port 19 at the end of channel 18 for inflating and deflating balloon 20, and ports 16 and 17 being in this example, two inflow segment ports in communication with the main infusion channel 15. Channel 18 includes a connection which incorporates a valve 18a for maintaining the balloon 20 in an inflated state as well as for deflating the balloon 20 when appropriate.

Figure 5:
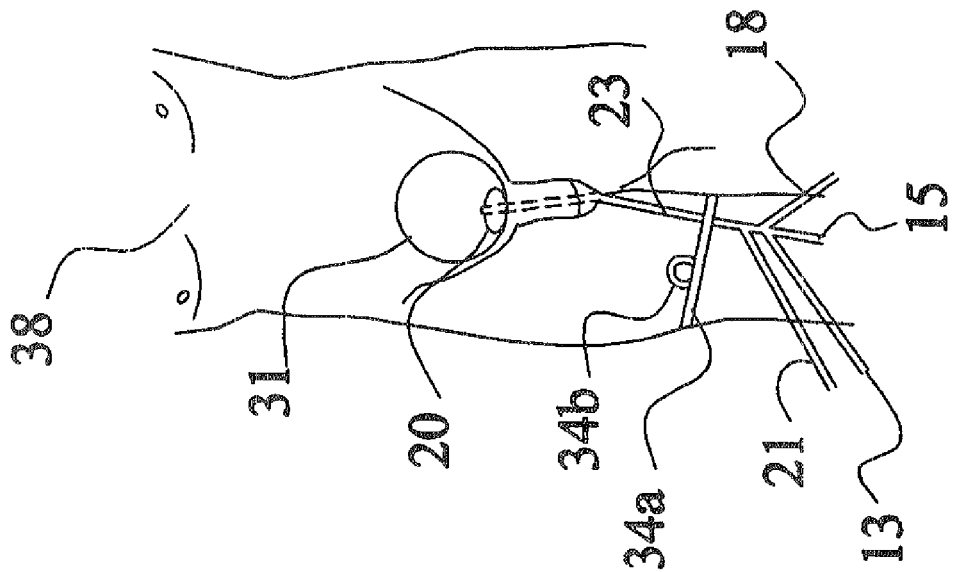
FIG. 5 is a conceptual depiction of the inventive catheter attached to a male patient.

FIG. 4 is a conceptual depiction of the inventive catheter attached to a female patient 30 as further depicted in FIG. 1 and FIG. 5 is a conceptual depiction of the inventive catheter attached to a male patient 38.

The pressure sensor channel 21 and the transducer port 22 are in communication (electrical or electro/mechanical) with the computer processing system 5 and the automatic pump 7 so as to monitor and maintain the desired pressure within the bladder. The automatic processing system is configured so as to be easily overridden should the physician determine it necessary to immediately relieve the pressure being held in the bladder as previously discussed herein.

As discussed above, the manual override control function can be programmed to be operated from the keyboard 3 or the display 2 itself can be a touch control display, such as those typically seen in restaurants computer systems, or a separate associated hardware component control can be incorporated such that when functionally activated, the programming will recognize the override function being activated to allow for the physician to take over control of the procedure. An override control device may be a switch or relay device or other means incorporated in the display monitor, keyboard or hardware and is depicted in FIG. 1 as 32 at three different optional locations as examples of how to incorporate such a feature.

It should be understood that the preceding is merely a detailed description of one or more embodiments of this invention and that numerous changes to the disclosed embodiments can be made in accordance with the disclosure herein without departing from the spirit and scope of the invention. The preceding description, therefore, is not meant to limit the scope of the invention. Rather, the scope of the invention is to be determined only by the appended claims and their equivalents.

What is claimed is:

1. A urological medical system for performing a controlled hydrodistention of the urinary bladder for treating a bladder dysfunction problem, the system comprising:
    central microprocessing means configured to facilitate an automatic control of a treatment procedure to be performed on a patient, said central microprocessing means further comprising means for entering data related to the treatment procedure, means for printing out desired procedure documentation data, and means for displaying desired parameters related to the procedure;
    a saline solution fluid source;
    fluid warmer means in fluid communication with said saline solution fluid source for varying a temperature of said saline solution fluid;
    pump means in fluid communication with the fluid warmer means, configured to pump said saline solution through a corresponding catheter saline solution infusion channel into a bladder of the patient to be treated;

a catheter system comprising a catheter having the saline solution infusion channel having one or more fluid inlet ports at a distal end of the catheter configured to be inserted in the bladder, a medicine infusion channel adapted to be connected to a tube in fluid communication with a syringe, a balloon near the distal end of the catheter system and channel means for inflating and deflating said balloon within the bladder, and pressure sensor channel means configured to monitor a pressure within the bladder during a treatment procedure, said pressure sensor channel means further including sensor means near the distal end of the catheter system for transmitting bladder pressure data to the central microprocessing means; and means for securing said syringe, which is adapted to be in fluid communication with the medicine infusion channel of the catheter system, to a limb of a patient being treated.

2. The system according to claim 1, wherein the desired parameters related to the procedure include fluid infusion rate, volume infused, pressure in the bladder and procedure time.

3. The system according to claim 1, wherein the pump means is in electronic controlled communication with the central microprocessing means so as to pump the saline solution fluid at a desired preset infusion rate, monitor a volume infused into the bladder and to create controlled pressure inside the bladder so that said controlled pressure will not exceed a desired level.

4. The system according to claim 1, further comprising:
mobile equipment support platform means for supporting the central microprocessing means, said fluid warmer means, and said pump means.

5. The system according to claim 4, further comprising:
vertically adjustable tube holder means adapted on said mobile equipment support platform means, said vertically adjustable tube holder means for adjusting a height of a tube containing said saline solution fluid being infused in said bladder so that said tube is capable of being located in a generally level orientation at a desired height.

6. The system according to claim 1, wherein the central microprocessing means further comprises:
manual override means for stopping the inflow of fluid into the bladder, for increasing fluid volume in the bladder, for terminating the procedure, for changing the infusion rate of the saline solution fluid and for changing an infusion time.

7. The system according to claim 1, wherein the means for securing said syringe to the limb of the patient being treated comprises:
a first strap portion being of sufficient length to be wrapped around the patient's limb and secured thereon;
a second strap portion, an intermediate portion thereof being fixed to an intermediate portion of the first strap portion, said second strap portion being of sufficient length to be wrapped around said syringe so that said syringe is tangentially secured to said first strap portion;
fastening means for securing said first strap portion to said limb and fastening means for securing said syringe within second strap portion; and
means for slidingly engaging the catheter within the first strap portion.

8. The system according to claim 7, wherein said fastening means for securing said first strap portion to said limb and fastening means for securing said syringe within second strap portion are mating hook and loop fasteners.

9. The system according to claim 7, wherein said first strap portion includes an intermediate elastic portion for stretching said first strap portion or said second strap portion includes an intermediate elastic portion for stretching said second strap portion or said first and second strap portions each include an intermediate elastic portion for stretching said corresponding first and second strap portions.

10. The system according to claim 7, wherein the means for slidingly engaging the catheter within the first strap portion comprises:
a clip fixed to said first strap portion, said clip being adapted to slidingly engage the catheter.

11. The system according to claim 1, further comprising means for the temporary automatic stopping of the pump when the pressure in the bladder reaches a predetermined maximum level.

* * * * *